United States Patent [19]

Guth

[11] Patent Number: 4,735,968

[45] Date of Patent: Apr. 5, 1988

[54] METHOD OF TREATING TINNITUS WITH AOAA

[75] Inventor: Paul S. Guth, New Orleans, La.

[73] Assignee: Tulane Educational Fund, New Orleans, La.

[21] Appl. No.: 937,460

[22] Filed: Dec. 2, 1986

Related U.S. Application Data

[63] Continuation of Ser. No. 741,347, Jun. 5, 1985, abandoned.

[51] Int. Cl.$^4$ .................................... A61K 31/195
[52] U.S. Cl. ................................................ 514/561
[58] Field of Search ..................................... 514/561

[56] References Cited

U.S. PATENT DOCUMENTS 3,284,210 11/1966 Rosenberg ............................ 99/2
4,123,538 10/1978 Umen .................................. 424/319

OTHER PUBLICATIONS

Hazell: Measurement of Tinnitus in Humans in Evered and Lawrence (eds.), Tinnitus, London, England, Pitman Books, 1981, pp. 35–53.
Tibbles JAR, McGreal DA: Trial of Amino-Oxyacetic Acid, an Anticonvulsant, Can. Med. Ass. J. 1963; 88: 881–886.
LaVeck et al.: Anticonvulsant Properties of Amino-Oxyacetic Properties of Amino-Oxyacetic Acid, J. New Drugs 1962; 2:160–166.
Bobbin et al.: Effects of Amino-Oxyacetic Acid on Cochlear Potentials and Preyer Reflex, Nature (Lond.) 1969; 223: 70–71.
Melding et al.: The Use of Intravenous Lidocaine in the Diagnosis and Treatment of Tinnitus, J. Laryngol Otol. 1978: 92: 115–121.
Bobbin et al.: An Examination of an Electrochemical Mechanism for Noise-Induced Hair Cell Loss: Noise with Amino-Oxyacetic Acid (AOAA), Trans Am Acad Ophthalmol Otolaryngol 1976; 82:299–304, Transcript.

Primary Examiner—Albert T. Meyers
Assistant Examiner—John M. Kilcoyne
Attorney, Agent, or Firm—Nixon & Vanderhye

[57] ABSTRACT

Tinnitus symptoms are treated with aminooxyacetic acid (AOAA) administered orally at dosages of 200–300 mg/day. Clinically significant reductions in tinnitus symptoms were observed.

2 Claims, No Drawings

METHOD OF TREATING TINNITUS WITH AOAA

This is a continuation of application Ser. No. 741,347 filed June 5, 1985, now abandoned.

This invention relates to a method of treating tinnitus in which an effective quantity of amino-oxyacetic acid (AOAA) is administered to a patient experiencing tinnitus and his/her symptoms are alleviated.

Tinnitus is the perception of sound in the absence of acoustic stimulus and may be of the buzzing, ringing, whistling or hissing quality or it may involve more complex sounds that vary over time. Tinnitus may be intermittent or continuous and an associated hearing loss may also be present. Tinnitus may occur as a symptom of nearly all ear disorders. The mechanism involved in the production of tinnitus has not previously been explained. Although no specific medical or surgical therapy is reported for tinnitus in *The Merck Manual*, 14th edition (1982), it is suggested that patients may find relief by playing background music to mask the tinnitus.

We have successfully used AOAA as a palliative in the treatment of human tinnitus. AOAA does not itself cause tinnitus, as does aspirin, for example.

Amino-oxyacetic acid (AOAA) is a known compound and has been used primarily as an inhibitor of the catabolism of the inhibitory neurotransmitter γ-aminobutyric acid (GABA). As such it was subjected to clinical trials as an anticonvulsant in the 1960's; see Canada Med. Ass. J. 1963, 881–886 and J New Drugs 1962; 2:160–166. U.S. Pat. No. 4,123,538 to Uman describes substituted compounds related to AOAA as antisecretory compositions, cardiotonic agents and calcium binding agents while U.S. Pat. No. 3,284,210 to Rosenberg describes animal feed suppliments and feed compositions to enhance animal growth and improve feed efficiency containing, among other materials, substituted compounds related to AOAA.

We have discovered, and hereby disclose, that amino-oxyacetic acid (AOAA) and the pharmaceutically acceptable salts thereof, particularly the hemihydrochloride, are useful as a palliative in the treatment of human tinnitus.

The amount of AOAA administered and the dosage regime will be determined by the clinician. Being a known compound about which there is considerable clinical experience, the limits of tolerance and toxicity are available as benchmarks for initial therapy. We have found amounts of AOAA in the range of 100 to up to 300 mg/day, in divided doses, i.e., 3 or 4 equally divided doses per day, to be effective in providing an acceptable degree of relief to patients suffering from tinnitus. Therapy may be continued solely as the tinnitus symptoms exist. Hearing is restored to its previous level at the end of one week of treatment.

The route of administration may be one of convenience selected by the clinician; oral administration in the form of an oral dosage unit such as a tablet, capsule or liquid, is preferred. AOAA may be used as the acid or as a pharmaceutically acceptable salt or ester.

Testing of drugs for use in treating tinnitus is notoriously difficult. Tinnitus has multiple etiologies not always known, is a fluctuating phenomenon, and patients are often taking other drugs, such as an antidepressants and aspirin, concurrently. In addition, they may be using tinnitus maskers. If asked to stop other medication and the use of a masker and/or hearing aid, the baseline mindset, anxiety and irritability change. Compounding these difficulties is the possibility of a placebo response. Because the drug seemed to have a cochlear site of action, patients were initially selected for study if their audiograms were indicative of cochlear lesions, and they enjoyed a reduction in tinnitus following intravenous lidocaine reported as "lidocaine positive".

The method of the present invention will be illustrated with reference to the following clinical investigation.

CLINICAL EXAMPLES

Preliminary screening: Patients were either middle aged men, or women without child-bearing potential, chosen from amongst a population of private patients reporting severe tinnitus. Following favorable results from a history, physical, complete blood count, urinalysis, SMA-12 liver screen and stool guaiac, patients were admitted to the trial.

The patients were then given lidocaine (1–2 mg/kg, intravenously) over a 3–4 minute period and asked to report whether the lidocaine affected their tinnitus; they were scored lidocaine positive if their tinnitus seemed reduced. An EKG monitor, means to assist respiration and diazepam were available at the time of lidocaine administration.

Patients were then given the following tests: electronystagmography, puretone audiometry, speech audiometry, short increment sensitivity index, tone decay, impedance testing, acoustic reflex testing, and tinnitus matching. Of those so examined ten patients were selected as meeting all criteria, including a positive response to lidocaine. An additional five patients (four lidocaine-negative, one not having received lidocaine) were also allowed to participate in the drug trial, but were not considered the primary experimental population.

Therapy: Patients qualifying for testing were then given a week's supply of either (1) AOAA 25 mg/capsule, and told to take 2 capsules four times a day, or (2) an identically matching placebo and told to follow the same schedule. The active drug and placebo were distributed randomly and in a two week double-blind, crossover design, so that each patient was administered AOAA for one week followed by placebo for one week, or placebo for one week followed by AOAA for one week.

Discussion of Results: A summary of our observations is given in the following tables reporting the subjects' characteristics (TABLE I) and a summary of improved speech discrimination scores of 3 of the subjects.

Of these ten lidocaine-positive patients, three reported subjective lessening in tinnitus during the week in which they took AOAA but not during the placebo week. Interestingly, all three had an etiology of sudden hearing loss. One additional patient, not having received lidocaine, also reported a lessening of tinnitus while on AOAA. One of the three whose tinnitus was decreased and two other patients, not reporting subjective reduction in tinnitus, had significant improvements in speech discrimination during AOAA treatment (TABLE II). Note that patient #9's discrimination score reverted towards control level during the post-drug placebo week.

We also observed that two patients (one lidocaine positive, one lidocaine negative, #4, 15, TABLE I), failed to report a reduction in tinnitus during the week of AOAA treatment but in the subsequent placebo week reported that their tinnitus seemed worse. While uncertainty does exist it may have been that AOAA reduced the tinnitus so gradually that the improvement went unnoticed. Upon withdrawal from AOAA the patients reported what they perceived to be a worsening of tinnitus.

Two patients (one lidocaine positive, one lidocaine negative) reported a subjective reduction in tinnitus during the placebo week. An additional four patients who were lidocaine-negative and one not receiving lidocaine, were also allowed in the AOAA drug trial at a dosage of 200 mg/day. Only one of these, the patient not receiving lidocaine, #1, reported a lessening of tinnitus.

One of the four patients reporting a reduction in tinnitus had had a longstanding diplacusis which went unrecognized until given AOAA (subject #2) when the diplacusis remitted.

Three patients exhibited an improvement in speech discrimination scores and these are highlighted in TABLE II.

TABLE I

| | | Subject Characteristics | | | |
|---|---|---|---|---|---|
| subject | Daily Dosage | Etiology | Lidocaine | ΔDiscrim. (see Table II) | ΔTinnitus (↑ inc. tin.) (↓ dec.tin.) |
| 10 | 300 mg. | Trauma | + | — | — |
| 8 | 300 mg. | ? | + | — | — |
| 5 | 200 mg. | ? | + | — | — |
| 4 | 200 mg. | ? | + | — | ↑ Placebo |
| 1 | 200 mg. | ? | + | — | ↓ Placebo |
| 7 | 200 mg. | ? | + | ↑ AOAA | — |
| 9 | 300 mg. | ? | + | ↑ AOAA | — |
| 3 | 200 mg. | Sudden HL | + | ↑ AOAA | ↓ AOAA |
| 6 | 300 mg. | Sudden HL | + | — | ↓ AOAA |
| 2 | 100 mg. | Sudden HL | + | — | ↓ AOAA, ↓ diplacusis |
| 11 | 200 mg. | Noise | not tested | — | ↓ AOAA |
| 12 | 200 mg. | ? | — | — | — |
| 13 | 200 mg. | ? | — | — | — |
| 14 | 200 mg. | Meniere's | — | — | ↓ Placebo |
| 15 | 200 mg. | Noise | — | — | ↑ Placebo |

TABLE II

| | Improvement in Speech Discrimination Scores During AOAA Treatment | | |
|---|---|---|---|
| Subject # | Speech Discrim. Pre-Test | Speech Discrim. After Week 1 | Speech Discrim. After Week 2 |
| 3 | Right ear 68% Left ear DNT | Right ear 60% Left ear - (placebo) | Right ear 84% Left ear - (AOAA) |
| 7 | Right ear 60% Left ear 68% | Right ear 72% Left ear 72% (placebo) | Right ear 92% Left ear 92% (AOAA) |
| 9 | Right ear 48% Left ear 100% | Right ear 76% Left ear 100% (AOAA) | Right ear 56% Left ear 100% (placebo) |

Two of the above-noted patients did not report any subjective improvement in tinnitus. There were changes in tinnitus matching in some patients, but as has been previously reported (in Hazell, J.W.P., Measurement Of Tinnitus In Humans in Evered, D.E., and Lawrenson, G. (editors), Tinnitus, London, England, Pitman Books (1981) pp. 35–53), these were inconsistent and not easily interpretable.

After having had experience with six of the original ten patients at a dosage level 200 mg/day it became clear that this dosage schedule produced neither complaints nor signs of toxicity. In the last four patients of this series the dosage schedule was raised to 300 mg/day by asking patients to take 3 capsules four times a day. Again the drug produced no toxicity, so an additional four patients were given 400 mg/day in four divided doses. At this dose level there were complaints of dizziness, lightheadedness, disequilibrium, some nausea and headache. The results with these four patients are not included in this report because they did not last the entire course of treatment. No consistent changes were seen in any of the other tests, including the audiometric, ENG and clinical laboratory tests.

We claim:

1. A method of treating tinnitus in a person experiencing same comprising orally administering to said person amino-oxyacetic acid or amino-oxyacetic hemihydrochloride in an amount from about 100 to 300 mg/day.

2. The method of claim 1 in which the amino-oxyacetic acid is administered in 3 or 4 equally divided doses per day.

* * * * *